(12) United States Patent
Bess et al.

(10) Patent No.: US 9,517,099 B2
(45) Date of Patent: Dec. 13, 2016

(54) SYSTEM FOR CORRECTIVE SPINAL SURGERY AND METHOD OF USE

(71) Applicant: K2M, Inc., Leesburg, VA (US)

(72) Inventors: Robert Shay Bess, Castle Rock, CO (US); Frank Schwab, New York, NY (US); David Dreusicke, Herndon, VA (US); Theo Choi, Arlington, VA (US); Thomas Errico, New York, NY (US)

(73) Assignee: K2M, Inc., Leesburg, VA (US)

( * ) Notice: Subject to any disclaimer, the term of this patent is extended or adjusted under 35 U.S.C. 154(b) by 0 days.

(21) Appl. No.: 14/541,222

(22) Filed: Nov. 14, 2014

(65) Prior Publication Data

US 2015/0142067 A1    May 21, 2015

Related U.S. Application Data

(60) Provisional application No. 61/904,800, filed on Nov. 15, 2013.

(51) Int. Cl.
  *A61B 17/70* (2006.01)
  *A61B 17/88* (2006.01)

(52) U.S. Cl.
  CPC ......... *A61B 17/8894* (2013.01); *A61B 17/708* (2013.01); *A61B 17/7086* (2013.01)

(58) Field of Classification Search
  CPC . A61B 17/88; A61B 17/8875; A61B 17/8886; A61B 17/8894
  USPC ................... 606/300–321, 86 A, 96, 99, 104
  See application file for complete search history.

(56) References Cited

U.S. PATENT DOCUMENTS

| 7,278,995 | B2 | 10/2007 | Nichols et al. |
| 8,235,997 | B2 | 8/2012 | Hoffman et al. |
| 8,308,774 | B2 | 11/2012 | Hoffman et al. |
| 8,388,659 | B1 | 3/2013 | Lab et al. |
| 2005/0192579 | A1 | 9/2005 | Jackson |

(Continued)

FOREIGN PATENT DOCUMENTS

WO   2013170262 A2   11/2013

OTHER PUBLICATIONS

Extended European Search Report dated Jul. 22, 2015 issued in European Application No. 14 19 3216.

(Continued)

*Primary Examiner* — Ellen C Hammond
*Assistant Examiner* — Christina Negrellirodrigue
(74) *Attorney, Agent, or Firm* — Carter, DeLuca, Farrell & Schmidt, LLP (57) ABSTRACT

A pedicle screw locking system includes a reduction tube and a locking driver. The reduction tube includes an inner shaft, a pair of grips, a reduction sleeve, and a rotatable tube. The inner shaft has a threaded end and reduction arms distally extending from the threaded end. Each grip of the pair of grips has a finger configured to engage the receiver of a pedicle screw. The reduction sleeve and the rotatable tube are disposed over and coaxially aligned with the inner shaft. The rotatable tube is coupled to the reduction sleeve. The rotatable tube moves the reduction sleeve relative to the reduction arms. The locking driver includes a threaded portion and a blunt tip. The threaded portion is configured to thread into threads in the receiver of the pedicle screw until the blunt tip locks the receiver of the pedicle screw.

24 Claims, 7 Drawing Sheets

(56) References Cited

U.S. PATENT DOCUMENTS

| | | | |
|---|---|---|---|
| 2006/0111712 A1* | 5/2006 | Jackson | A61B 17/7037 |
| | | | 606/914 |
| 2006/0200132 A1 | 9/2006 | Chao et al. | |
| 2008/0045970 A1* | 2/2008 | Saidha | A61B 17/8615 |
| | | | 606/104 |
| 2009/0292308 A1 | 11/2009 | Jones et al. | |
| 2011/0118791 A1* | 5/2011 | Nunley | A61B 17/7086 |
| | | | 606/279 |
| 2011/0245881 A1 | 10/2011 | Mitchell | |
| 2012/0022594 A1 | 1/2012 | Walker et al. | |
| 2012/0046699 A1 | 2/2012 | Jones et al. | |
| 2012/0191144 A1 | 7/2012 | Peultier et al. | |
| 2013/0018419 A1 | 1/2013 | Rezach et al. | |
| 2013/0030445 A1 | 1/2013 | Dauster et al. | |
| 2013/0046344 A1 | 2/2013 | Nunley et al. | |
| 2013/0184763 A1 | 7/2013 | McClintock et al. | |
| 2014/0100583 A1* | 4/2014 | Butler | A61B 17/7082 |
| | | | 606/104 |

OTHER PUBLICATIONS

Partial European Search Report dated Apr. 21, 2015 issued in European Application No. 14193216.

* cited by examiner

SYSTEM FOR CORRECTIVE SPINAL SURGERY AND METHOD OF USE

CROSS-REFERENCE TO RELATED APPLICATIONS

This application claims the benefit of, and priority to, U.S. Provisional Patent Application Ser. No. 61/904,800, which was filed on Nov. 15, 2013, the entire contents of the above application is hereby incorporated herein by reference.

BACKGROUND

1. Technical Field

The present disclosure relates to a system and method for operating on the spine. More particularly, the present disclosure relates to a system and method for manipulating vertebrae during assembly of a corrective spinal construct.

2. Discussion of Related Art

The spinal column is a complex system of bones and connective tissues that provide support for the human body and protection for the spinal cord and nerves. The adult spine has an upper and a lower portion. The upper portion contains 24 discrete bones, which are subdivided into three areas including 7 cervical vertebrae, 12 thoracic vertebrae and 5 lumbar vertebrae. The lower portion is comprised of the sacral and coccygeal bones. The cylindrical shaped bones, called vertebral bodies, progressively increase in size from the upper portion downwards to the lower portion.

An intervertebral disc along with two posterior facet joints cushion and dampen the various translational and rotational forces exerted upon the spinal column. The intervertebral disc is a spacer located between two vertebral bodies. The facets provide stability to the posterior portion of adjacent vertebrae. The spinal cord is housed in the canal of the vertebral bodies. It is protected posteriorly by the lamina. The lamina is a curved surface with three main protrusions. Two transverse processes extend laterally from the lamina, while the spinous process extends caudally and posteriorly. The vertebral bodies and lamina are connected by a bone bridge called the pedicle.

The spine is a flexible structure capable of a large range of motion. There are various disorders, diseases, and types of injury which restrict the range of motion of the spine or interfere with important elements of the nervous system. The problems include, but are not limited to scoliosis, kyphosis, excessive lordosis, spondylolisthesis, slipped or ruptured discs, degenerative disc disease, vertebral body fracture, and tumors. Persons suffering from any of the above conditions typically experience extreme or debilitating pain and often times diminished nerve function. These conditions and their treatments can be further complicated if the patient is suffering from osteoporosis, or bone tissue thinning and loss of bone density.

Spinal fixation apparatuses are widely employed in surgical processes for correcting spinal injuries and diseases. When the disc has degenerated to the point of requiring removal, there are a variety of interbody implants that are utilized to take the place of the disc. These include polyetheretherketone ("PEEK") interbody spacers, metal cages, and cadaver and human bone implants. In order to facilitate stabilizing the spine and keeping the interbody in position, other implants are commonly employed, including longitudinally linked rods secured to coupling elements, which in turn are secured to the bone by spinal bone fixation fasteners such as pedicle screws, hooks, and others. The opposing pair of longitudinally linked rods is commonly disposed along the long axis of the spine via a posterior approach. Pedicle screws are utilized to capture these rods and can be manufactured from any biocompatible material, including cobalt chrome, stainless steel, titanium, and PEEK. It is desired to perform these procedures in a minimally invasive manner to minimize pain and reduce recovery time for the patient.

SUMMARY

In an aspect of the present disclosure, a pedicle screw locking system includes a reduction tube and a locking driver. The reduction tube includes an inner shaft, a pair of grips, a reduction sleeve, and a rotatable tube. The inner shaft has a threaded end and reduction arms that extend distally from the threaded end. An outer surface of each reduction arm defines a groove. A distal end of each grip of the pair of grips includes a finger. Each grip of the pair of grips is received within the groove of one of the reduction arms. Each finger is configured to engage a receiver of a pedicle screw. The reduction sleeve is disposed over and coaxially aligned with the inner shaft. The reduction sleeve is radially fixed relative to the inner shaft. The rotatable tube is disposed over and coaxially aligned with the threaded end of the inner shaft. The rotatable tube is coupled to the proximal end of the reduction sleeve. The rotatable tube moves the reduction sleeve relative to the reduction arms. The locking driver includes a locking shaft that defines a proximal end and a distal end. The distal end of the locking shaft includes a threaded portion and a blunt tip extending from the threaded portion. The locking shaft is insertable through the reduction tube and is configured to lock the pedicle screw engaged by the pair of grips.

In aspects of the present disclosure, the rotatable tube is rotatably coupled to the proximal end of the reduction sleeve. The rotatable tube may be rotated about the threaded end of the inner shaft to move the reduction sleeve relative to the reduction arms.

In aspects of the present disclosure, the pedicle screw locking system includes a release button received within a button opening of the rotatable tube. The button opening is a blind hole orthogonal to the longitudinal axis of the rotatable tube. The release button includes a shaft slot that receives the threaded end of the inner shaft therethrough. In embodiments, the shaft slot includes a threaded portion configured to engage the threaded end of the inner shaft. In some embodiments, the release button has a first position such that the threaded portion is engaged with the threaded end of the inner shaft to engaged the threaded end of the inner shaft to move the reduction sleeve over relative to the reduction arms and a second position where the threaded portion is spaced-apart from the threaded end of the inner shaft. The rotatable tube may include a button biasing member that urges the release button towards the first position.

In aspects of the present disclosure, the inner shaft defines a recess between the threaded end and the reduction arms and each of the pair of grips includes a ring portion. The ring portion of each grip of the pair of grips is received within the recess to longitudinally fix each grip of the pair of grips relative to the inner shaft. The reduction sleeve may retain the pair of grips within the grooves of the reduction arms. The reduction arms may define a reduction slot therebetween.

In aspects of the present disclosure, the locking driver includes a handle that defines an opening. The proximal end of the locking shaft may be received within the opening of the handle. The opening and the proximal end may be shaped such that the locking shaft cooperates with the rotation of the handle.

In aspects of the present disclosure, a method for locking a pedicle screw includes, engaging a receiver of a pedicle screw with fingers of a pair of grips of a reduction tube, inserting a locking shaft through the reduction tube, and threading a threaded portion of the locking shaft into threads in the receiver of the pedicle screw until a blunt tip of the locking shaft engages a portion of the pedicle screw to lock the pedicle screw.

In aspects of the present disclosure, the method includes manipulating the reduction tube to reposition a vertebra engaged by the pedicle screw while the pedicle screw is locked by the locking shaft. The method may include unthreading the locking shaft from the receiver of the pedicle screw to unlock the pedicle screw.

In aspects of the present disclosure, the method includes inserting a spinal rod through a reduction slot defined between the reduction arms. The method may include seating the spinal rod into the receiver of the pedicle screw. Seating the spinal rod may include rotating the rotatable tube about the inner shaft. The method may include securing the spinal rod to the receiver of the pedicle screw with a set screw after the spinal rod is seated.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, wherein.

DETAILED DESCRIPTION

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" will refer to the portion of the device or component thereof that is closer to the clinician and the term "distal" will refer to the portion of the device or component thereof that is farther from the clinician. In addition, the term "cephalad" is used in this application to indicate a direction toward a patient's head, whereas the term "caudad" indicates a direction toward the patient's feet. Further still, for the purposes of this application, the term "lateral" indicates a direction toward a side of the body of the patient, i.e., away from the middle of the body of the patient. The term "posterior" indicates a direction toward the patient's back, and the term "anterior" indicates a direction toward the patient's front. Additionally, in the drawings and in the description that follows, terms such as front, rear, upper, lower, top, bottom, and similar directional terms are used simply for convenience of description and are not intended to limit the disclosure.

Figure 1:
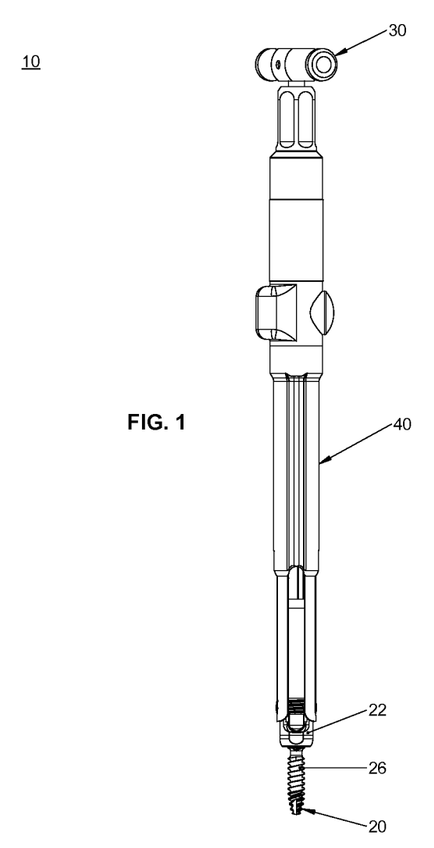
FIG. 1 is a side view of an embodiment of a pedicle screw locking system provided in accordance with the present disclosure engaged with a pedicle screw.
Figure 1A:
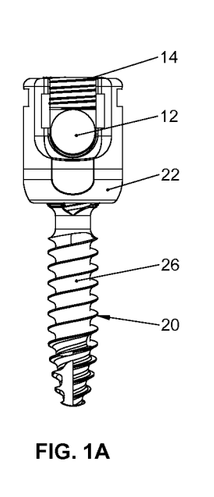
FIG. 1A is a side view of the pedicle screw of FIG. 1 with a spinal rod secured in a receiver of the pedicle screw with a set screw.

Referring to FIGS. 1 and 1A, an exemplary embodiment of a pedicle screw locking system 10 provided in accordance with the present disclosure includes a locking driver 30 and a reduction tube assembly 40. The locking system 10 is configured to engage a pedicle screw 20 having a receiver 22 and a threaded shank 26. The receiver 22 is moveable relative to the threaded shank 26. The receiver 22 has a U-shaped channel configured to receive a spinal rod 12 and includes a set screw 14 that is configured to secure the spinal rod 12 to the receiver 22 of the pedicle screw 20 and lock the receiver 22 relative to the threaded shank 26. The receiver 22 may partially deform when the set screw 14 secures the spinal rod 12 and locks the receiver 22. Such a pedicle screw is disclosed in commonly owned U.S. Patent Pub. Nos. 2009/0292308 and 2012/0046699, the entire contents of each are incorporated by reference herein.

Figure 2:
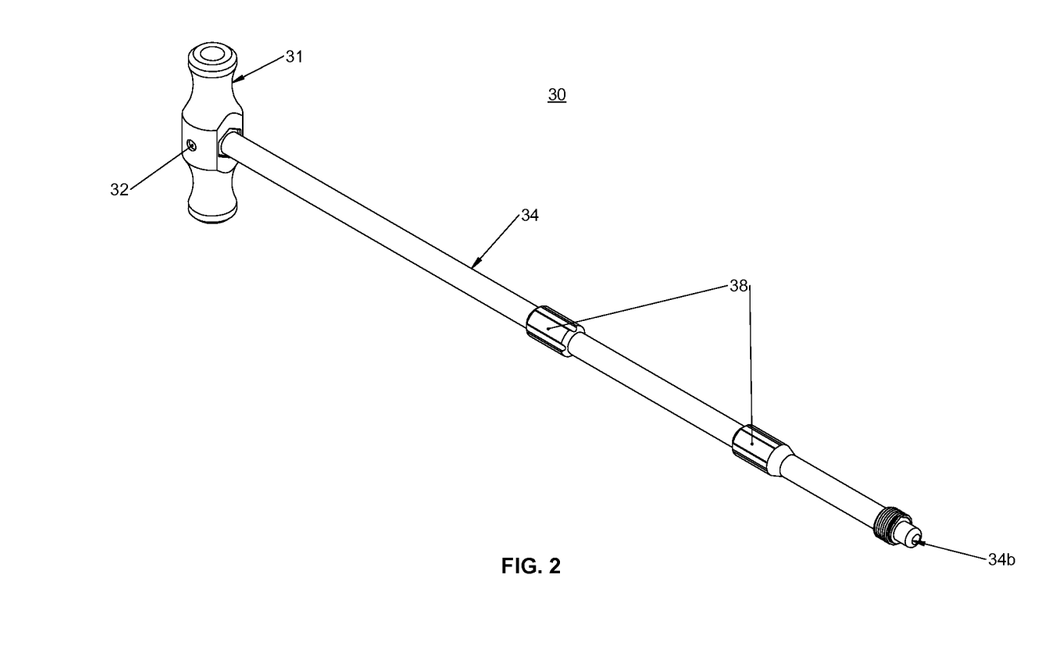
FIG. 2 is a perspective view of the locking driver of the pedicle screw locking system of FIG. 1.
Figures 3, 4:
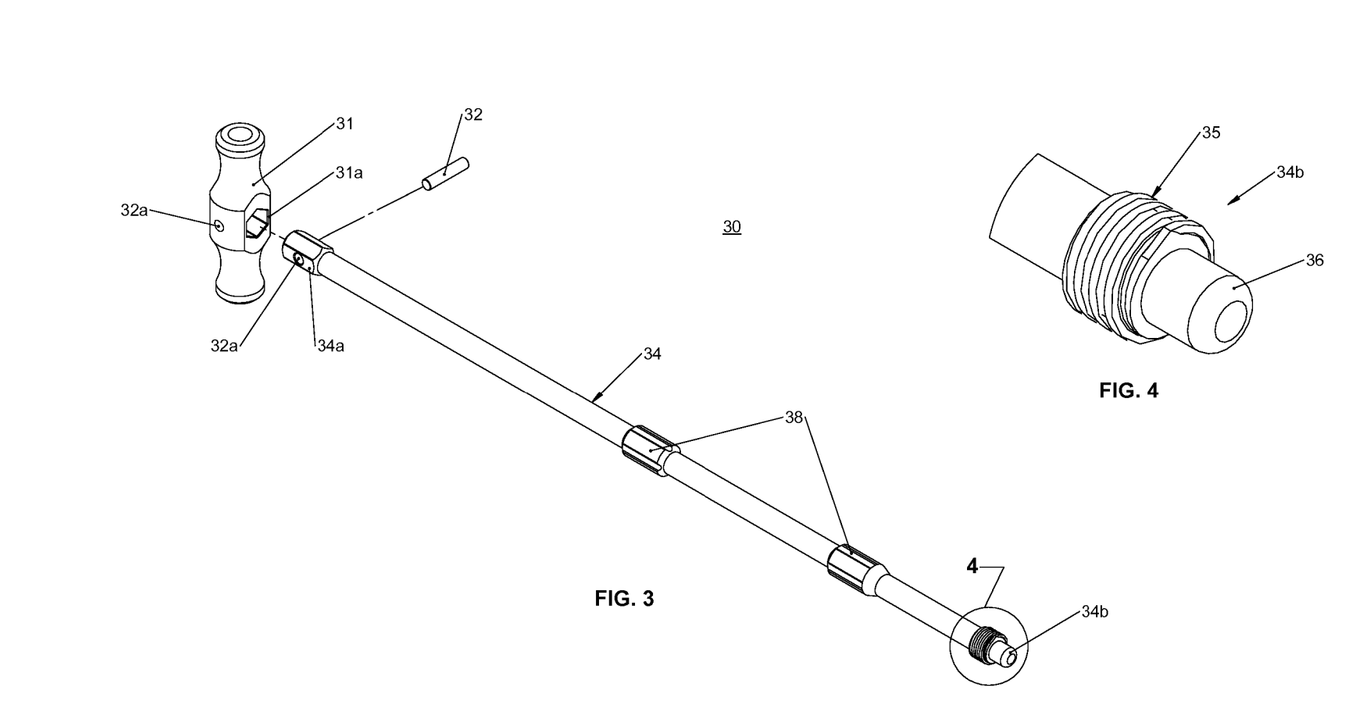
FIG. 3 is an exploded view, with parts separated, of the components of the locking driver shown in FIG. 2.
FIG. 4 is an enlargement of the detail area 4 shown in FIG. 3.

Referring to FIGS. 2-4, the locking driver 30 includes a handle 31, a handle pin 32, and a locking shaft 34. The handle 31 includes an opening 31a. The locking shaft 34 defines a proximal end 34a and a distal end 34b. The opening 31a of the handle 31 receives the proximal end 34a of the locking shaft 34. The opening 31a may be shaped to receive the proximal end 34a such that the locking shaft 34 cooperates with the rotation of handle 31. As shown in FIG. 3, the opening 31a and the proximal end 34a are hexagonal in shape; however, it is contemplated that the opening 31a and the proximal end 34a may be in a wide variety of shapes including triangular shaped, rectangular shaped, pentagonal shaped, octagonal shaped, decagonal shaped, star shaped, etc. The proximal end 34a and the handle 31 may include pin holes 32a for slidably receiving a handle pin 32 to retain the handle 31 on the proximal end 34a of the locking shaft 34. In embodiments, the handle pin 32 engages the locking shaft 34 to rotate the handle 31.

It is contemplated that the locking driver may be used with any rod reduction system and/or pedicle screw having a receiver for receiving a spinal rod and a set screw. Such rod reduction systems are disclosed in commonly owned U.S. Patent Pub. Nos. 2011/0087298, 2011/0118791, 2013/

0046344, and 2013/0184763, the entire contents of each are incorporated by reference herein.

With particular reference to FIG. 4, the distal end 34b of the locking shaft 34 includes a threaded portion 35 and a blunt tip 36. The threaded portion 35 is configured to engage threads 23 (FIG. 11) in the receiver 22 (FIG. 1) of the pedicle screw 20. The threaded portion 35 may include square threads; however, it is contemplated that the threaded portion 35 may include any suitable threads for engaging the threads 23 in the receiver 22. The blunt tip 36 extends distally from the threaded portion 35 and is configured to engage the threaded shank 26 (FIG. 1) as detailed below. In embodiments, the locking shaft 34 may include shoulders 38 configured to engage the reduction tube assembly 40 as detailed below.

Figure 7:
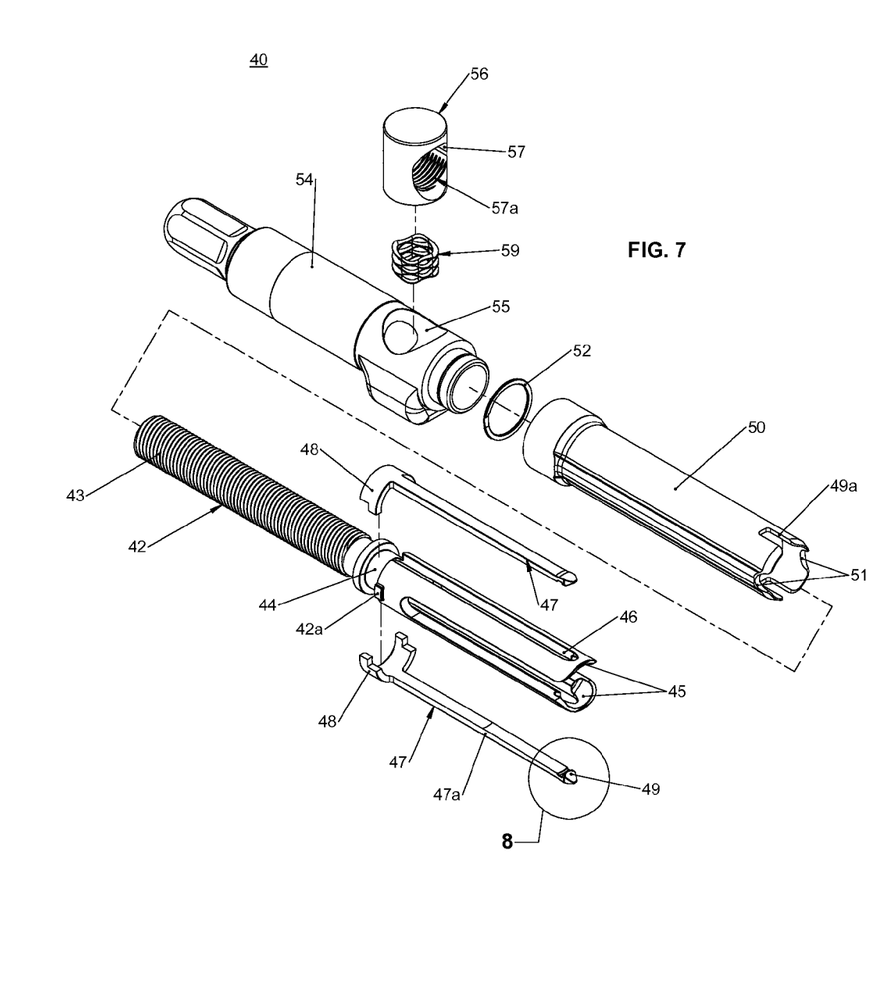
FIG. 7 is an exploded view, with parts separated, of the components of the reduction tube shown in FIG. 5.
Figure 8:
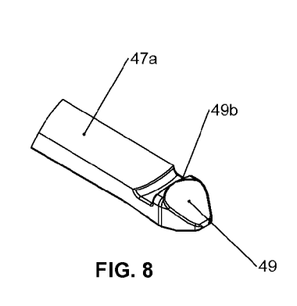
FIG. 8 is an enlargement of the detail area 8 shown in FIG. 7.

With reference to FIGS. 5-8, the reduction tube assembly 40 includes an inner shaft 42, a pair of grips 47, a reduction sleeve 50, a rotatable tube 54, and a release button 56. The reduction tube assembly 40 defines a longitudinal through passage. The inner shaft 42 includes a proximal threaded end 43, a pair of reduction arms 45, and a recess 44 separating the threaded portion 43 from the reduction arms 45. The inner shaft 42 may include aligning tabs 42a adjacent the recess 44 for aligning the reduction sleeve 50 with the inner shaft 42. The pair of reduction arms 45 define a through reduction slot 45a (FIG. 9) therebetween that is configured to receive a spinal rod 12 (FIG. 1A). Each of the pair of reduction arms 45 includes a groove 46 in an outer surface thereof. Each of the pair of grips 47 includes a grip arm 47a, a ring portion 48, and a finger 49. The ring portion 48 is adjacent a proximal end of the grip arm 47a and the finger 49 is adjacent a distal end of the grip arm 47a. The grip arm 47a of a respective one of the pair of grips 47 is received within the groove 46 of a respective one of the pair of reduction arms 45. The ring portion 48 of each of the pair of grips 47 is received within the recess 44 of the inner shaft 42 to longitudinally fix the pair of grips 47 relative to the inner shaft 42. Each ring portion 48 may include features to interlock the ring portion 48 of the other one of the pair of grips 47 as best shown in FIG. 7. The fingers 49 include an engagement surface 49b for engaging a surface 28 (FIG. 11) of the pedicle screw 20 as detailed below.

Figure 12:
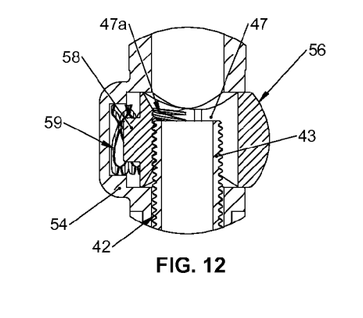
FIG. 12 is an enlargement of the detail area 12 shown in FIG. 10.

The proximal end of the reduction sleeve 50 is disposed over the distal end of the rotatable tube 54. A retaining ring 52 may be positioned between the reduction sleeve 50 and the rotatable tube 54 to secure the reduction sleeve 50 to the rotatable tube 54. When the reduction sleeve 50 is secured to the rotatable tube 54, the rotatable tube 54 is rotatable relative to the reduction sleeve 50. The reduction sleeve 50 and the rotatable tube 54 may form a housing. The release button 56 is received within a button hole 55 of the rotatable tube 54 such that the release button 56 cooperates with the rotation of the rotatable tube 54. The button hole 55 may be a blind hole orthogonal to the longitudinal axis of the rotatable tube 54. The release button 56 includes a through shaft slot 57. The shaft slot 57 includes a threaded portion 57a configured to engage the threaded end 43 of the inner shaft 42 as shown in FIG. 12. The release button 56 may include a biasing member protrusion 58 (FIG. 12) configured to be inserted into the button hole 55. A button biasing member 59 is positioned around the biasing member protrusion 58 between the release button 56 and the rotatable tube 54 to bias the threaded portion 57a of the release button 56 into engagement with the threaded end 43 of the inner shaft 42 as detailed below and shown in FIG. 12.

The reduction sleeve 50 and the rotatable tube 54 are positioned over and coaxial with the inner shaft 42 such that the threaded end 43 is received through the shaft slot 57 of the release button 56. An inner surface of the reduction sleeve 50 may include alignment grooves (not shown) configured to receive the alignment tabs 42a of the inner shaft 42 to radially align the reduction sleeve 50 with the inner shaft 42. The proximal end of the reduction sleeve 50 may include rod recesses 51 configured to engage a spinal rod 12 (FIG. 1A) received within the reduction slot 45a (FIG. 9) when the reduction sleeve 50 is aligned with the inner shaft 42. When the reduction sleeve 50 is disposed over the inner shaft 42, the reduction sleeve 50 retains the ring portions 48 within the recess 44 and the grip arms 47a within the grooves 46. The distal end of the reduction sleeve 50 may include finger slots 49a positioned such that the fingers 49 may move outward to receive a portion of the receiver 22 of the pedicle screw 20 as detailed below.

Figures 5, 6:
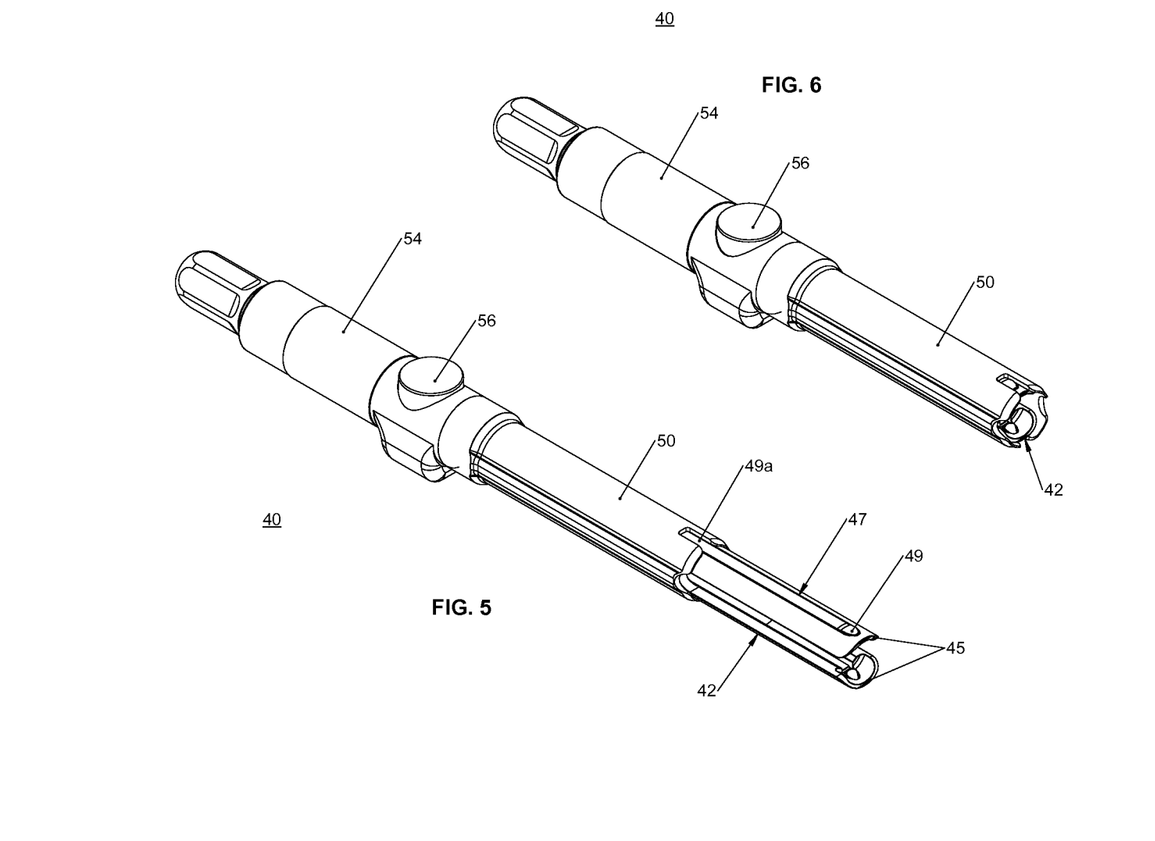
FIG. 5 is a perspective view of the reduction tube of the pedicle screw locking system of FIG. 1 in a first position.
FIG. 6 is a perspective view of the reduction tube of the pedicle screw locking system of FIG. 1 in a second position.

With reference to FIGS. 5, 6, and 12, the reduction sleeve 50 is moveable between a first position (FIG. 5) and a second position (FIG. 6). In the first position, the distal end of the reduction sleeve 50 is positioned over the inner shaft 42 adjacent the ring portions 48 (FIG. 7) of the pair of reduction arms 45. In the second position, the reduction sleeve 50 is disposed substantially over the reduction arms 45 of the inner shaft 42 such that the distal end of the reduction sleeve 50 is adjacent the fingers 49. The reduction sleeve 50 may be reduced from the first position towards the second position by the cooperation of the threaded portion 57a of the button 56 with the threaded end 43 of the inner shaft 42 when the rotatable tube 54 is rotated in a first radial direction relative to the inner shaft 42. Similarly, the reduction sleeve 50 may be retracted from the second position towards the first position by the cooperation of the threaded portion 57a of the button 56 with the threaded end 43 of the inner shaft 42 when the rotatable tube 54 is rotated in a second radial direction relative to the inner shaft 42.

The reduction sleeve 50 may also be reduced from the first position towards the second position by depressing button 56 against the button biasing member 59 to disengage the threaded portion 57a of the button 56 from the threaded end 43 of the inner shaft 42 and pushing the reduction sleeve 50 over the pair of reduction arms 45. Similarly, the reduction sleeve 50 may also be refracted from the second position towards the first position by depressing button 56 against the button biasing member 59 to disengage the threaded portion 57a of the button 56 from the threaded end 43 of the inner shaft 42 and pulling the reduction sleeve 50 away from the pair of reduction arms 45. It is contemplated that fine adjustments of the reduction sleeve 50, e.g., reduction and retraction, may be made by the rotation of the rotatable tube 54 and rapid or coarse adjustments of the reduction sleeve 50 may be completed by the depressing button 56 and repositioning the reduction sleeve 50 relative to the inner shaft 42.

Referring to FIGS. 1 and 9-14, the pedicle screw locking system 10 is used to lock the receiver 22 of the pedicle screw 20. Locking the receiver 22 may permit the repositioning of a vertebra engaged by the pedicle screw 20 to a desired position or correction before a spinal rod 12 (FIG. 1A) is secured within the receiver 22 of the pedicle screw 20.

Figure 9:
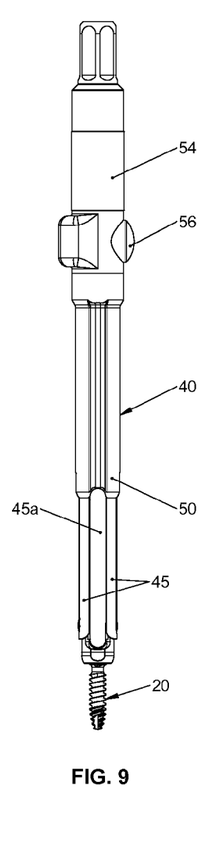
FIG. 9 is a side view of the reduction tube of FIG. 5 engaged with the receiver of a pedicle screw.
Figure 10:
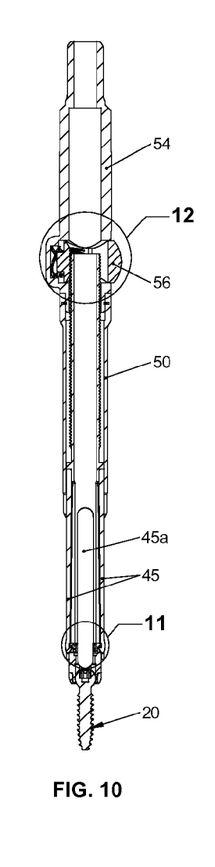
FIG. 10 is a side-longitudinal cross-sectional view taken along the longitudinal axis of the reduction tube of FIG. 9.
Figure 11:
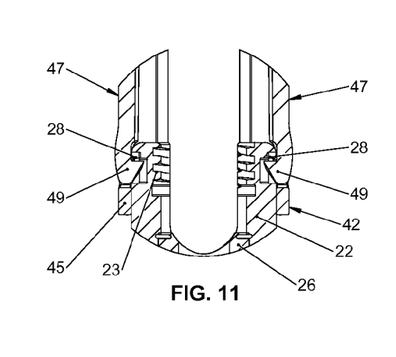
FIG. 11 is an enlargement of the detail area 11 shown in FIG. 10.

The receiver 22 of the pedicle screw 20 is locked by engaging the receiver 22 with the reduction tube assembly 40 as shown in FIGS. 9-11. The pair of reduction arms 45 are slid over the receiver 22 until the fingers 49 of the pair of grips 47 engage features of the receiver 22, e.g., the engagement surfaces 49b of the fingers 49 engaging surfaces 28 of the receiver 22. The fingers 49 may be displaced outward as the pair of reduction arms 45 are slid over the receiver 22.

Figure 13:
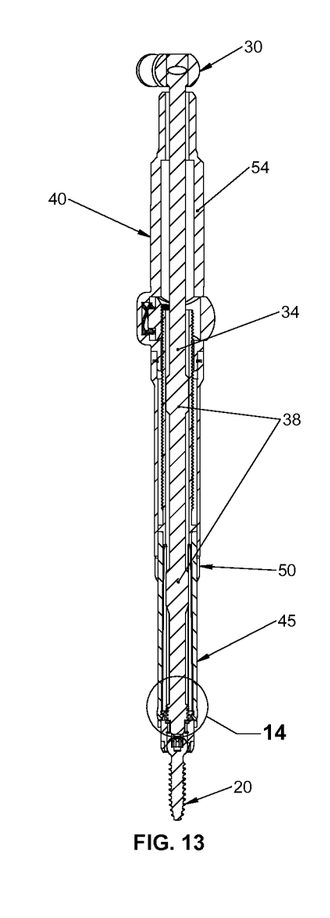
FIG. 13 is a side-longitudinal cross-sectional view taken along the longitudinal axis of the pedicle screw locking system of FIG. 1.
Figure 14:
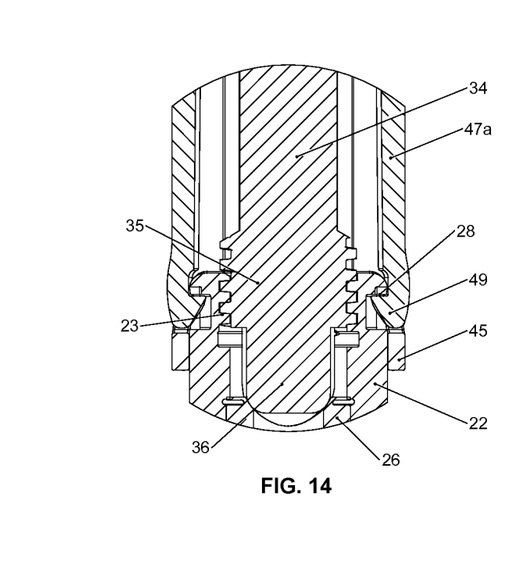
FIG. 14 is an enlargement of the detail area 14 shown in FIG. 13.

When the reduction tube assembly 40 is engaged with the receiver 22, the locking shaft 34 of the locking driver 30 is inserted through the reduction tube assembly 40 as shown in FIG. 13. The shoulders 38 of the locking shaft 34 may engage inner surfaces of the reduction tube assembly 40 to coaxially align the locking shaft 34 with the reduction tube assembly 40. The handle 31 may be rotated to engage the threaded portion 35 of the locking shaft 34 with threads of the receiver 22. The threaded portion 35 engages the threads 23 of the receiver 22 until the blunt end 36 engages the threaded shank 26 as shown in FIG. 14. When the blunt end 36 engages the threaded shank 26 the receiver 22 is locked relative to the threaded shank 26 locking the orientation of the pedicle screw 20. When the pedicle screw 20 is locked, the reduction tube assembly 40 may be manipulated to reposition or calibrate the vertebra engaged by the pedicle screw 20 to a desired position. Once the pedicle screw 20 and the vertebra are in the desired position, the locking driver 30 is unthreaded from the receiver 22 of the pedicle screw 20 to unlock the pedicle screw 20.

A spinal rod 12 (FIG. 1A) may be inserted through the reduction slot 45a after the locking driver 30 is withdrawn from the reduction tube assembly 40. The rotatable tube 54 of the reduction tube assembly 40 is then reduced to seat the spinal rod 12 into the receiver 22 of the pedicle screw 20. When the spinal rod 12 is seated into the receiver 22, a set screw 14 (FIG. 1A) is threaded into the threads 23 of the receiver 22 to secure the spinal rod 12 to the receiver 22. The receiver 22 may partially deform to lock the set screw 14 relative to the receiver 22.

Combining the locking driver 30 and the pedicle screw 20 allows for direct manipulation of the vertebra by the practitioner. By fixing a specific angle of the polyaxial pedicle screw 20 (i.e., the receiver 22 with respect to the shank 26), the combination allows for direct manipulation and correction of spinal deformities. As such, polyaxial pedicle screws 20 can be used in spinal constructs to allow for ease of rod insertion and rod capture while allowing for altering the mechanics of the polyaxial pedicle screw 20 such that the combination of the locking driver 30 and the polyaxial pedicle screw 20 are capable of simultaneously correcting deformities, manipulate the vertebra, and capture the spinal rod 12. The combination of the locking driver 30 and the polyaxial pedicle screw 20 may span several levels so that correction may be applied to several vertebrae where each vertebra has a locking driver 30 and polyaxial pedicle screw 20 coupled thereto. Additionally, the combination allows the capture of a spinal rod 12 that is specifically contoured to the deformity correction and bring the vertebral segments to the spinal rod 12 in sequential fashion and dissipates applied forces to reduce the force applied to a single vertebra during the deformity correction procedure. This reduces the likelihood of implant pull-out or failure.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope and spirit of the claims appended hereto.

What is claimed:

1. A pedicle screw locking system comprising:
    a reduction tube, including:
        an inner shaft having a threaded end and reduction arms extending distally from the threaded end, each reduction arm defining a groove in an outer surface thereof;
        a pair of grips each having a finger adjacent a distal end thereof, each grip of the pair of grips received within the groove of a respective reduction arm, each finger configured to engage a receiver of a pedicle screw;
        a reduction sleeve disposed over and coaxially aligned with the inner shaft, the reduction sleeve radially fixed relative to the inner shaft; and
        a rotatable tube disposed over and coaxially aligned with the threaded end of the inner shaft, the rotatable tube coupled to a proximal end of the reduction sleeve, the rotatable tube moving the reduction sleeve relative to the reduction arms; and
    a locking driver including a locking shaft defining a proximal end and a distal end thereof, the distal end of the locking shaft including a threaded portion and a blunt tip extending from the threaded portion, the locking shaft insertable through the reduction tube and configured to lock the pedicle screw engaged by the pair of grips.

2. The system of claim 1, wherein the rotatable tube is rotatably coupled to the proximal end of the reduction sleeve.

3. The system of claim 2, wherein the rotatable tube is rotated about the threaded end of the inner shaft to move the reduction sleeve relative to the reduction arms.

4. The system of claim 1 further comprising a release button received within a button opening of the rotatable tube, the button opening being a blind hole orthogonal to a longitudinal axis of the rotatable tube, the release button including a shaft slot that receives the threaded end of the inner shaft therethrough.

5. The system of claim 4, wherein the shaft slot includes a threaded portion configured to engage the threaded end of the inner shaft.

6. The system of claim 5, wherein the release button has a first position, wherein the threaded portion is engaged with the threaded end of the inner shaft such that as the rotatable tube is rotated the release button engages the rotatable tube to move the reduction sleeve relative to the reduction arms, and a second position, wherein the threaded portion is spaced-apart from the threaded end of the inner shaft.

7. The system of claim 6, wherein the rotatable tube includes a button biasing member urging the release button towards the first position.

8. The system of claim 1, wherein the inner shaft defines a recess between the threaded end and the reduction arms and each grip of the pair of grips includes a ring portion, the ring portion of each grip of the pair of grips received within the recess to longitudinally fix each grip of the pair of grips relative to the inner shaft.

9. The system of claim 1, wherein the reduction sleeve retains the pair of grips within the grooves of the reduction arms.

10. The system of claim 1, wherein the reduction arms define a reduction slot therebetween.

11. The system of claim 1, wherein the locking driver includes a handle defining an opening, the proximal end of the locking shaft received within the opening of the handle.

12. The system of claim 11, wherein the opening and the proximal end are shaped such that the locking shaft cooperates with rotation of the handle.

13. A method for locking a pedicle screw comprising:
engaging a receiver of a pedicle screw with fingers of a pair of grips of a reduction tube, the reduction tube including:
an inner shaft having a threaded end and reduction arms extending distally from the threaded end, each reduction arm defining a groove in an outer surface thereof, each grip of the pair of grips received within a respective groove;
a reduction sleeve; and
a rotatable tube; and
inserting a locking shaft through the reduction tube; and
threading a threaded portion of the locking shaft into threads in the receiver of the pedicle screw until a blunt tip of the locking shaft extending distally from the threaded portion engages a portion of the pedicle screw to lock the pedicle screw.

14. The method of claim 13 further comprising manipulating the reduction tube to reposition a vertebra engaged by the pedicle screw after the pedicle screw is locked by the locking shaft.

15. The method of claim 14 further comprising unthreading the locking shaft from the receiver of the pedicle screw to unlock the pedicle screw.

16. The method of claim 13 further comprising inserting a spinal rod through a reduction slot defined between the reduction arms.

17. The method of claim 16 further comprising seating the spinal rod inserted through the reduction slot into the receiver of the pedicle screw.

18. The method of claim 17, wherein seating the spinal rod includes rotating the rotatable tube about the inner shaft.

19. The method of claim 17 further comprising securing the spinal rod to the receiver of the pedicle screw with a set screw after the spinal rod is seated.

20. The method of claim 14, wherein manipulating the reduction tube positions the vertebra in a desired position.

21. A pedicle screw locking system comprising:
a rod reduction assembly including a pair of grips extending from a housing, the housing having a longitudinal passage therethrough and each grip of the pair of grips having a finger adjacent a distal end thereof configured to engage a receiver of a pedicle screw; and
a locking driver including a locking shaft defining a proximal end and a distal end thereof, the distal end of the locking shaft including a threaded portion and a blunt tip extending from the threaded portion, the locking shaft insertable through the longitudinal passage of the rod reduction device and the threaded portion configured to engage threads on the pedicle screw such that when the threaded portion engages the pedicle screw threads, the blunt tip locks the pedicle screw engaged by the pair of grips.

22. A pedicle screw locking system comprising:
a pedicle screw including a shank, a receiver moveable relative to the shank and configured to receive a spinal rod, and threads configured to receive a set screw to secure a spinal rod within the receiver and lock the pedicle screw such that the shank and the receiver are fixed relative to one another; and
a locking shaft defining a proximal end and a distal end thereof, the distal end of the locking shaft including a threaded portion and a blunt tip extending from the threaded portion, the threaded portion threadably coupled to the threads of the receiver of the pedicle screw, the blunt tip engaging the shank of the pedicle screw to lock the pedicle screw when the threaded portion is threadably coupled to the receiver.

23. A method for locking a pedicle screw comprising:
engaging a receiver of a pedicle screw with fingers of a pair of grips of a reduction device, the reduction device including a longitudinal passage therethrough;
inserting a locking shaft through the longitudinal passage of the reduction device; and
threading a threaded portion of the locking shaft into threads in the receiver of the pedicle screw until a blunt tip of the locking shaft distally extending from the threaded portion engages a portion of the pedicle screw to lock the pedicle screw.

24. A locking driver comprising:
a locking shaft defining a proximal end and a distal end thereof, the distal end of the locking shaft including a threaded portion and a blunt tip extending from the threaded portion, the threaded portion configured to threadably couple the locking shaft to a receiver of a pedicle screw and the blunt tip configured to engage a shank of the pedicle screw to lock the pedicle screw.

* * * * *